United States Patent [19]

Zavasnik et al.

[11] Patent Number: 5,085,211
[45] Date of Patent: Feb. 4, 1992

[54] PLASTER CAST MOLD AND LINER

[75] Inventors: Linda Zavasnik, 10 Lands End Rd., Travelers Rest, S.C. 29690; Philip L. Reid, Duncan, S.C.

[73] Assignee: Linda Zavasnik, Travelers Rest, S.C.

[21] Appl. No.: 571,087

[22] Filed: Aug. 22, 1990

[51] Int. Cl.$^5$ .............................. A61F 5/04
[52] U.S. Cl. .............................. 600/8; 128/98.1; 600/12; 600/24
[58] Field of Search ............ 128/83, 87 C, 89 R, 128/90, 89.1, 98.1, 112.1, 116, 120.1, 883, 891, 168; 264/DIG. 30; 428/314.4; 4/237-240

[56] References Cited

U.S. PATENT DOCUMENTS

| | | | |
|---|---|---|---|
| 3,671,981 | 6/1972 | Smith | 4/239 X |
| 4,213,211 | 7/1980 | Bemis et al. | 4/239 |
| 4,462,122 | 7/1984 | Broeils | 4/239 |
| 4,477,932 | 10/1984 | Lenosky | 4/239 |

OTHER PUBLICATIONS

Codman & Shurtleff Inc., Florence Orthopedic Stroller Chair, Journal of Bone and Joint Surgery, Sep. 1962, p. 34, vol. 44-A, #6.

Primary Examiner—Robert A. Hafer
Assistant Examiner—Brian E. Hanlon
Attorney, Agent, or Firm—Bailey & Hardaway

[57] ABSTRACT

An improved method and apparatus is disclosed for constructing a stronger body cast using a mold and a replaceable liner to provide a passage for the elimination of bodily wastes and to further protect the cast from being soiled by bodily wastes.

6 Claims, 2 Drawing Sheets

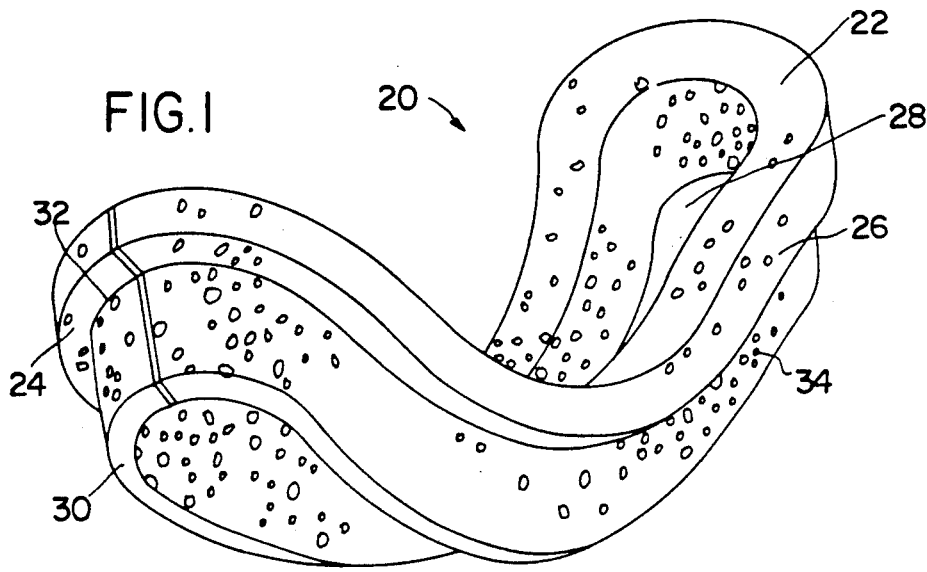
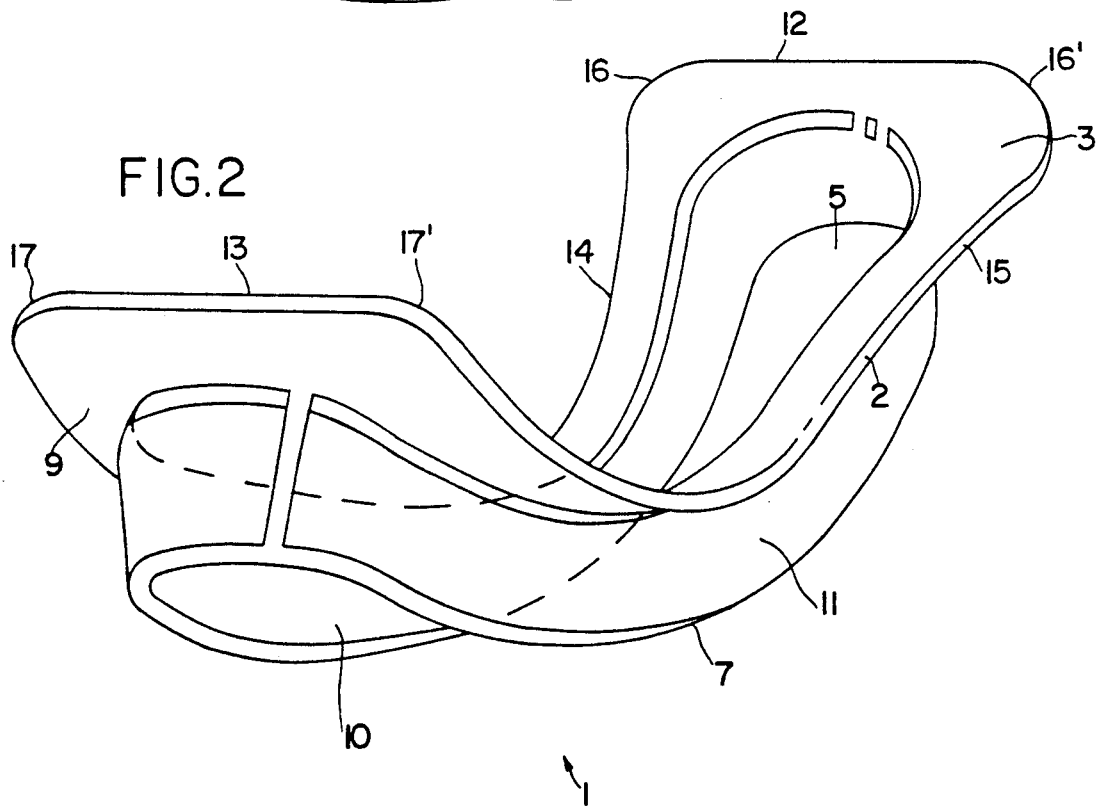

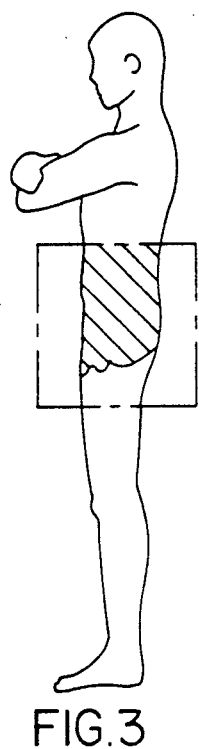
FIG.3
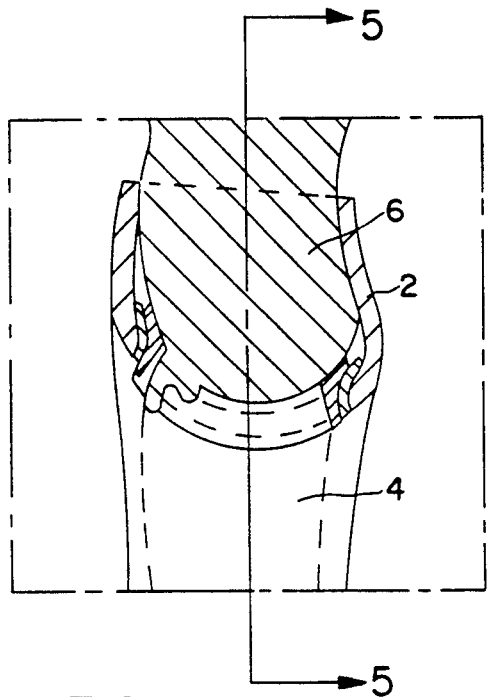
FIG.4
FIG.5
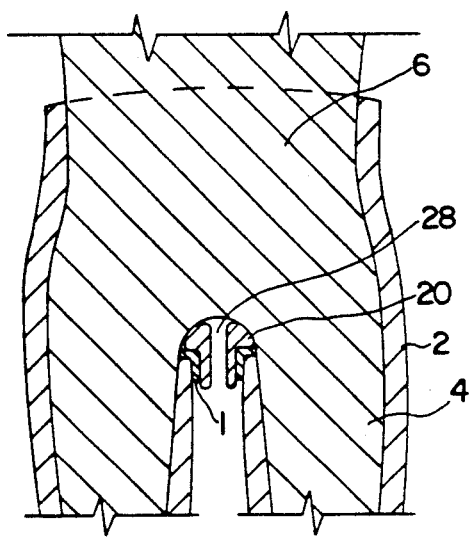
FIG.6
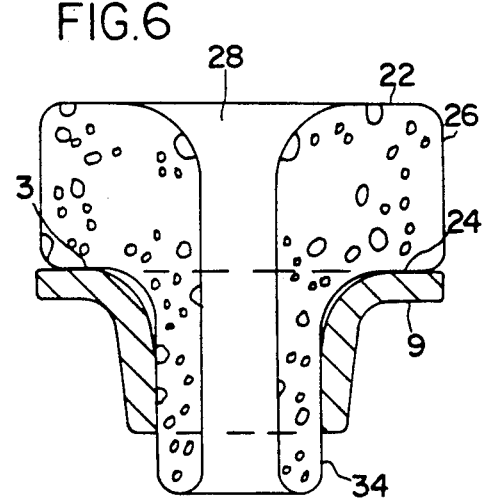

PLASTER CAST MOLD AND LINER

BACKGROUND OF THE INVENTION

This invention relates to the art of plaster casts and more particularly to the art of body casts.

Typical problems with body casts involve patient discomfort and lack of hygiene during the weeks or months a cast must be worn. A body cast as initially constructed covers the anal/genital region of a patient. After the cast hardens, a hole must be drilled or sawed into the cast to provide an opening for the elimination of the patient's bodily wastes. Inevitably, the cast becomes soiled by the patient's defecation and urination. As a result, the cast rapidly becomes unsanitary, unsightly, and develops an offensive odor which worsens with time.

To date there has been no effective way to avoid the soiling of a body cast. Larger cast openings would reduce the soiling but pose an increased risk of the cast breaking, while constant replacement of the cast would impair the treatment of the patient. Therefore, much room for improvement in the art exists.

SUMMARY OF THE INVENTION

It is thus an object of this invention to provide a method for installing a body cast against a mold which excludes plaster from the anal/genital regions, thereby eliminating the need of cutting an opening into the cast.

It is a further object of this invention to provide cast mold liners which are replaceable by the patient or the health care provider and which serve to protect the cast from soiling during the elimination of waste by the patient.

It is a further object of this invention to provide a cast mold which forms a protective dam around the anal/genital region of a patient and serves as a securing means for protective foam liners.

It is a still further object of this invention to provide a cast mold which strengthens a body cast and lessens the risk of accidental cast breakage.

BRIEF DESCRIPTION OF THE DRAWINGS

FIG. 1 is a perspective view of a liner used to protect the anal/genital opening of a body cast.

FIG. 2 is a perspective view of a cast mold used to construct a body cast which provides for an anal/genital opening.

FIG. 3 is a diagrammatic view of a human body showing the hip region.

FIG. 4 is an enlarged elevational view in cross section of a hip region of a patient with an attached body cast.

FIG. 5 is a front elevation view taken along line 5—5 of FIG. 4.

FIG. 6 is a transverse section of a body cast mold equipped with a liner.

DETAILED DESCRIPTION

In accordance with this invention, it has been found that a body cast can be constructed using a mold template equipped with a replaceable liner which protects the cast from contact with bodily wastes. Further, this mold excludes the patient's anal/genital area from being encroached by the cast material and thereby precludes the need for cutting an opening into the cast. Finally, this mold enables a cast to be constructed which is stronger than casts constructed by conventional means.

FIG. 1 shows a mold liner 20 detached from a cast mold 1 as seen in FIG. 2. The mold 1 includes an arcuate, oblong frame 2 with a uniform undersurface 3 and an outer surface 9, the frame defining a mold passage 5 in communication with the mold undersurface 3 and the outer surface 9. The frame 2 carries a sleeve 7 lining the mold passage 5 having an interior wall 10 and an exterior cast engaging wall 11 and extending downward in a near perpendicular fashion from the outer surface 9 of frame 2. The frame 2 is defined by a first parallel end wall 12 and a second parallel end wall 13 connected by a first symmetrical sidewall 14 and a second symmetrical side wall 15. A first pair of flared shoulders 16 and 16' is formed by the first sidewall 14 and the second sidewall 15 tapering in a divergent fashion to the first end wall 12. A second pair of shoulders 17 and 17' is similarly formed by the union of the sidewalls 14 and 15 with the second parallel end wall 13.

The compressible liner 20 includes a uniform liner undersurface 22 and a liner outer surface 24, collectively comprising a circumferential liner ridge 26. The liner 20 further defines a liner passage 28 in communication with the liner undersurface 22 and the liner outer surface 24, and a liner collar 30 attached to the outer liner surface 24 in a near perpendicular fashion and extending in a circumferential manner around a margin 32 of liner passage 28.

A body cast 2, seen in FIGS. 4 and 5, is constructed in accordance with the present invention by placing liner outer surface 24 of liner ridge 26 against the mold undersurface 3, as best seen in FIGS. 1, 2, and 6. An exterior liner collar surface 34 engages the mold inner sleeve surface 10. The mold and attached liner 20 is positioned around the genital span of a patient, the liner undersurface 22 in direct contact with the patient's skin and the liner passage 28 providing communication with the patient's anal/genital region. Temporary securing means such as tape or retaining straps are used to hold the mold 1 in place while simultaneously compressing the liner ridge 26 between the mold and the patient's skin. A typical body cast 2 is then constructed around the patient's hip region 6 and legs 4, the casting material placed against the cast engaging wall 11 and mold outer surface 9. The mold functions as a dam, excluding cast material from the liner passage 28 and mold passage 5. As a result, unobstructed communication with the anal/genital region of the patient is provided by the cast construction method. Upon curing of the cast, the temporary securing means may be removed.

The flared shoulders 16, 16', 17 and 17' and parallel end walls 12 and 13 of the mold, as shown in the preferred embodiment seen in FIG. 2, provide additional engaging and support means for securing the mold to the cast. Since the cast is formed against and supported by a solid mold, the cast is stronger than traditional body casts. Further, the mold passage 5 obviates the need to cut an opening into a cured cast, eliminating an inherent structural weakness in the prior art casts.

During elimination of bodily waste, the liner 20 shields both the cast 2 and the mold 1 from contact with the waste. Liner ridge 26 forms a compressive seal with the skin and prevents migration of waste along the liner/skin interface. As a result, the majority of the waste exits through the liner sleeve 28. The portion of wastes which directly contacts the liner does not contaminate the cast and is easily removed by the replacement of the disposable liner.

The liner 20 is preferably constructed of a resilient, compressible, non-absorptive material such as closed cell foam and are supplied in sizes to accommodate different sized molds. For purposes of sanitation and ease of handling, the liners are designed to be disposable and can be changed by the patient without assistance. Removal requires only a gentle pull or tug of the liner directed away from the patient's body. The liner is replaced with a fresh liner, to conform to the appropriate sized mold, by the manual compression and insertion of the liner ridge 26 in the gap between the cast mold and the skin. The compressive force of the liner ridge 26 against the patient's skin is sufficient to secure the liner yet still enable blood circulation. While it is envisioned that the cast mold 1 and mold liner 20 will be used together, it is noted that the use of the cast mold alone offers a substantial improvement over the prior art. The use of the rigid mold not only strengthens the cast, but eliminates the need for cutting an opening into the cast. In addition, the use of the mold alone would offer some degree of protection against soiling the cast.

Likewise, a compressible liner could be used in a conventional cast without the benefit of a mold. The liner could be inserted and compressed between the patient's skin and the cast, offering some measure of cast protection. However, the combination of both the cast mold and the liner offers the highest level of patient comfort and hygiene.

While the mold could be of a flexible material, the preferred embodiment is of a rigid material such as plastic. The use of the rigid, arcuate mold strengthens the cast by providing a substantially immobile support around which the cast hardens and further eliminates the need for a subsequent opening to be cut into the cast.

Since most body cast patients are young children, one sized unisex molds would suffice for most users. However, larger molds reflecting differences in patient size or gender could be easily provided.

While the present invention is directed to plaster body casts, it is understood that other cast material, such as fiberglass, could be employed as well.

It is thus seen that the instant invention provides a method and apparatus for constructing a stronger body cast using a cast mold fitted with a replaceable liner. It is further seen that the invention protects the cast from being soiled by the patient's bodily wastes. Finally, the use of the cast mold eliminates the need for cutting an opening into the cured cast. As many variations are apparent to one of skill in the art from reading the above specification, such variations are within the spirit and scope of the instant invention as defined by the following appended claims.

That which is claimed:

1. A mold for use with a full pelvic to provide an opening around an anal/genital region of a patient, said mold for use between said pelvic cast and said anal/genital region and constructed so as to include a single place of substantially rigid material comprising:
   an arcuate oblong frame having a uniform undersurface and an outer surface, said frame defining a mold passage in communication with said undersurface and said outer surface;
   a sleeve, lining said mold passage, and extending in a near perpendicular fashion from said outer surface.

2. The apparatus of claim 1 wherein said frame has a first and a second parallel end wall, and a first and a second symmetrical side wall;
   a first pair of flared shoulders formed by said first and said second sidewall tapering in a divergent fashion to said first end wall;
   a second pair of flared shoulders formed by said first and said second sidewall tapering in a divergent fashion to said second end wall.

3. The apparatus according to claim 1 wherein said mold is constructed of plastic.

4. A compressible liner for use between a full pelvic cast and an anal/genital region to protect said anal/genital region of said cast comprising:
   a uniform liner undersurface and a liner outer surface, said undersurface and said outer surface collectively defining a circumferential liner ridge, said liner defining a liner passage in communication with said undersurface and said outer surface;
   a collar, attached to said outer liner surface in a near perpendicular fashion and extending in a circumferential manner around a margin of said liner passage.

5. The apparatus as recited in claim 4 wherein said liner is constructed of closed cell foam.

6. A method of building a cast against a mold and having a replaceable liner comprising the steps of:
   (a) selecting a mold which conforms to a dimension of a patient; and
   (b) positioning a liner against said mold; and
   (c) applying said mold with said liner affixed, to an anal/genital region of said patient, said liner in intimate contact with a skin surface of said patient and said mold forming a protective dam surrounding said anal/genital region of said patient;
   (d) compressing said liner against said patient; and
   (e) constructing a cast against said mold carrying said liner; and
   (f) curing said cast; and
   (g) removing said liner from said cast when said liner becomes soiled; and
   (h) installing a new foam liner between said mold and said skin surface; and
   (i) Repeating step g through h as required for patient comfort and hygiene.

* * * * *